United States Patent [19]

Moore

[11] Plant 4,454

[45] Aug. 21, 1979

[54] MINIATURE ROSE PLANT

[76] Inventor: Ralph S. Moore, 2519 E. Noble Ave., Visalia, Calif. 93277

[21] Appl. No.: 935,733

[22] Filed: Jun. 21, 1978

[51] Int. Cl.[2] ..... A01H 5/00

[52] U.S. Cl. ..... Plt./10

[58] Field of Search ..... Plt./10

*Primary Examiner*—Robert E. Bagwill

[57] ABSTRACT

The subject of the present disclosure is a new and distinct variety of miniature rose plant characterized by the brilliant red color of the flowers and by the profusion of bloom.

6 Drawing Figures

1

The present invention relates to a new and distinct variety of hardy, dwarf, bush type rose plant of the miniature class; the variety being primarily characterized — as to novelty — by deep red buds and bright red flowers which in general color effect are similar to Sarabande, a Floribunda variety (U.S. Plant Pat. No. 1,761, expired).

The variety is further characterized by:

An abundance of bloom, with flowers usually borne several to the stem in loose clusters.

Sweet light fragrance.

A plant which is vigorous, of rounded somewhat upright shape with semi-glossy to matt, small foliage with pointed leaflets; the buds and flowers being similar in form and size to Carol-Jean (miniature — U.S. Plant Pat. No. 4,254), but averaging less petals.

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Red Pinocchio (U.S. Plant Pat. No. 812, expired) as the seed parent and Little Chief (miniature — not patented), as the pollen parent.

Subsequent to origination of the variety I successfully reproduced it, at Sequoia Nursery located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

Variety name: BORN FREE.

Flowers borne: Usually several together in clusters of 3–5 or more on slender wirey stems.

2

Quantity of bloom: Abundant both outside and in greenhouse.

Bud:

*Peduncle.*—Medium to short length; slender but sturdy; erect; medium green, sometimes tinted bronze (outdoors).

*Hairs.*—Fairly numerous.

*Before calyx breaks.*—Size — small. Form short; pointed with several foliaceous apendages and numerous tiny hairs on surface of bud; with foliaceous parts extending beyond the tip of the bud equal to one-half or less of its length. Color — medium green, occasionally tinted with bronze (outdoors).

*As calyx breaks.*—Color — deep red — near Currant Red 821/1, sometimes lighter red near base with white area at base.

*Opening.*—Opens well in all weather.

Bloom:

*Size when fully open.*—small, averaging about 35–40 mm (1½").

*Petalage.*—Double — averaging about 20 petals, arranged regularly plus sometimes several small petaloids.

*Form.*—Cupped at first, becoming more open in the center, with petals reflexing loosely outward, and later at maturity, open and rolled loosely outward and downward. Open flowers show stamens.

Petals: Fairly thick; satiny on inside and on outside surface.

*Shape.*—Outside petals, broad lanceolate with rounded tip plus very small (short) acute tip.

*Intermediate.*—Broad lanceolate with rounded tip.

*Inside.*—Lanceolate with rounded tip.

Color: Newly opened flower from a plant grown outdoors (August 1978), Visalia, Calif.

*Outside petals.*—Outside surface — near Currant Red 821/1 (with both lighter and darker areas) and having a blueish tint on basal portion of petal with small white area at base. Inside surface — near Geranium Lake 20 or 20/1, overlaid or veined with darker shades and showing a blueish cast or tint near base with a small white area at base.

*Intermediate petal.*—Outside surface — similar to outside petal. Inside surface — similar to outside petal.

*Inner petal.*—Outside surface — same as intermediate petal; inside surface — same as intermediate petal.

*General color effect.*—Newly opened flowers — rich glowing geranium red. Three days open — color similar to newly opened flowers but less brilliant. Behavior — open well in all weather. Color lasts better than most other red miniatures. Spent petals drop off. Flower longevity (May 1978) — plant in pot 6–8 days or longer. Cut flowers at living room temperature 4–5 days or longer.

Reproductive organs:

*Stamens.*—Abundant, arranged regularly about pistils.

*Filaments.*—Varying length, fairly long, yellow.

*Anthers.*—Well formed; yellow.

*Pollen.*—Moderate amount.

*Pistils.*—Average number.

*Styles.*—Fairly even; medium to short length; bunched; color — greenish.

*Ovaries.*—All enclosed in calyx.

*Hips.*—Some.

*Sepals.*—Permanent; spear shaped; recurved against peduncle.

*Seed.*—Few or none.

Foliage:

*Leaves.*—Compound of five (sometimes three or seven) leaflets; fairly small; leathery; semi-glossy to matt.

*Leaflets.*—Shape: broad, nearly oval; apex acute; base rounded or rounded acute. Margin serrate.

*Color.*—Medium to dark green; new growth — normal (medium) green.

*Rachis.*—Medium strength; upper side may have a few tiny short prickles or hairs, grooved; underside sparsely thorny with few or no tiny prickles.

*Stipules.*—Medium long; narrow to medium width; medium length; narrow points which turn out usually at about 45 degrees.

Growth:

*Habit.*—Dwarf; bushy; rounded; much branched.

*Growth.*—Free vigorous; internodes short.

*Canes.*—Medium; slender; sturdy.

*Main stems.*—Color: medium green.

*Thorns.*—Average; slender; hooked slightly downward; color, brown. Prickles — none. Hairs — none.

*Branches.*—Color: medium green. Thorns: moderate number; medium length; slender; nearly straight, inclined downward. Medium oval base. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, substantially as illustrated and described, characterized by buds and flowers of a rich red color, being of a shade generally near Geranium Lake 20 or 20/1, the bud and flower resembling the variety Carol-Jean (U.S. Plant Pat. No. 4,254) in form and size but having less petals than Carol-Jean; and further characterized by a plant of vigorous and compact growth habit, easy to propagate from cuttings or by budding, with an abundance of small to medium size semi-glossy foliage and an abundance of flowers borne usually in loose clusters of 3 to 5 or more.

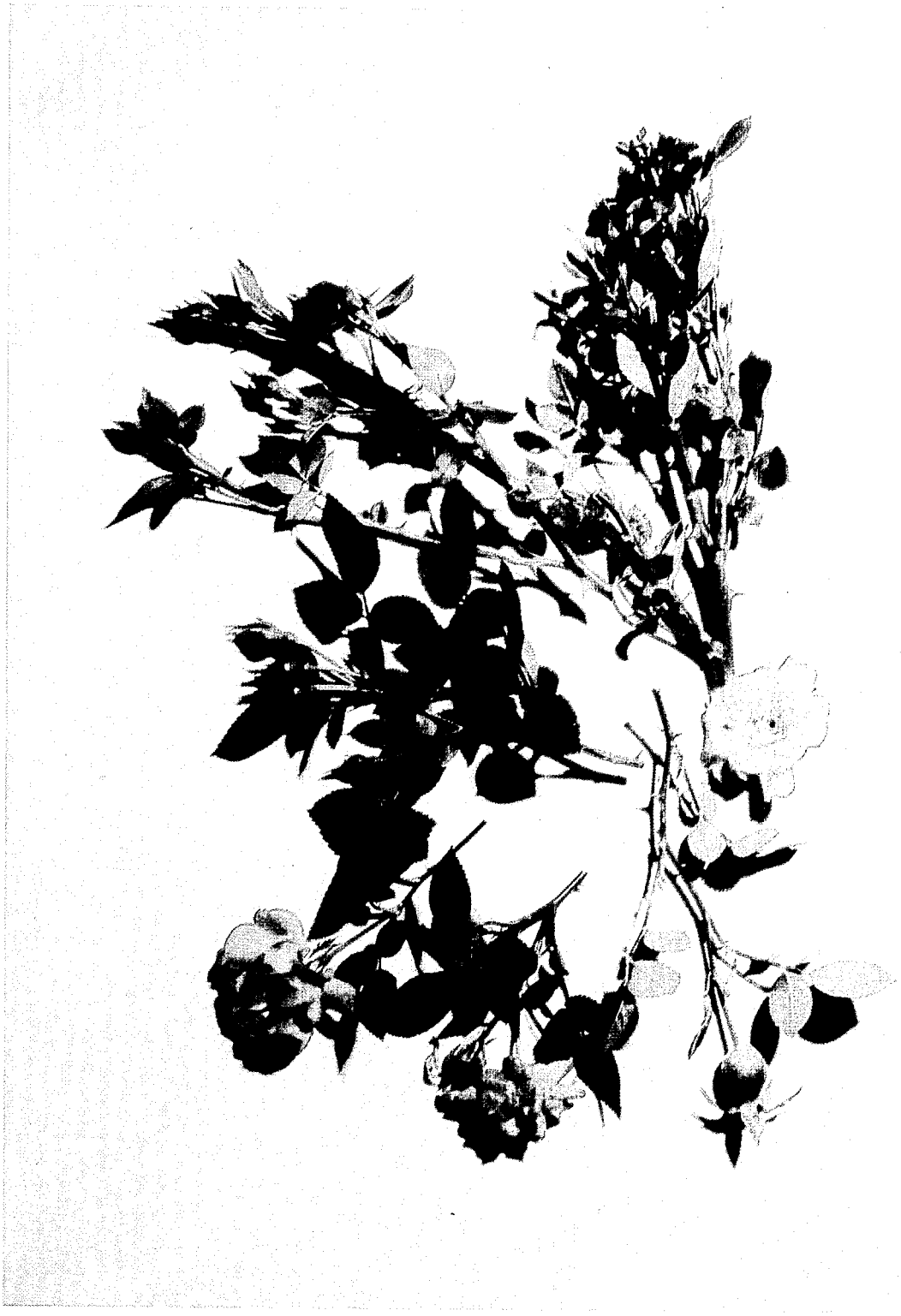

* * * * *